US00PP26333P3

(12) United States Plant Patent
de Ruiter

(10) Patent No.: US PP26,333 P3
(45) Date of Patent: Jan. 19, 2016

(54) ***RHIPSALIS* PLANT NAMED 'RUITSWEET'**

(50) Latin Name: *Rhipsalis clavata*
Varietal Denomination: RUITSWEET

(71) Applicant: Jacco de Ruiter, Nieuwerkerk a/d IJssel (NL)

(72) Inventor: Jacco de Ruiter, Nieuwerkerk a/d IJssel (NL)

( * ) Notice: Subject to any disclaimer, the term of this patent is extended or adjusted under 35 U.S.C. 154(b) by 82 days.

(21) Appl. No.: 13/999,378

(22) Filed: Feb. 18, 2014

(65) Prior Publication Data

US 2015/0237786 P1 Aug. 20, 2015

(51) Int. Cl.
*A01H 5/12* (2006.01)

(52) U.S. Cl.
USPC ..... Plt./372

(58) Field of Classification Search
USPC ..... Plt./372
See application file for complete search history.

*Primary Examiner* — Susan McCormick Ewoldt
(74) *Attorney, Agent, or Firm* — Cassandra Bright

(57) ABSTRACT

A new and distinct *Rhipsalis* cultivar named 'RUITSWEET' is disclosed, characterized by strong basal shoot production, prolific branching, compact and study form, and unique Greyed-Red color, especially in the sun. The new variety is a *Rhipsalis*, typically produced as an ornamental plant.

2 Drawing Sheets

Latin name of the genus and species: *Rhipsalis clavata.*
Variety denomination: 'RUITSWEET'.

BACKGROUND OF THE INVENTION

This application relates to a new cultivar of *Rhipsalis*. The new variety is the product of chance discovery, by the inventor, Jacco de Ruiter. The new variety originated as a naturally occurring whole plant mutation from the unpatented commercial variety *Rhipsalis clavata.*

The new variety was first selected by the inventor, in the breeder's commercial greenhouse in Nieuwerkerk, Netherlands during 2009. After identifying the new variety as a potentially interesting selection, the inventor continued confidential testing and propagation of 'RUITSWEET', assessing stability of the unique characteristics of this variety.

Asexual reproduction of the new cultivar 'RUITSWEET' was first performed at the breeder's commercial greenhouse in Nieuwerkerk, Netherlands by vegetative cuttings in 2010. Access to all plants was restricted, as plants were kept in a greenhouse not open to the public. Through subsequent propagation, around 6 generations have been reproduced, which have shown that the unique features of this cultivar are stable and reproduced true to type.

SUMMARY OF THE INVENTION

The cultivar 'RUITSWEET' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RUITSWEET'. These characteristics in combination distinguish 'RUITSWEET' as a new and distinct *Rhipsalis* cultivar:

1. Strong basal shoot production.
2. Prolific branching.
3. Compact and study plant.

4. Unique greyed-red flushing along branches, and at nodes, especially in sunny conditions.

PARENT COMPARISON

Plants of the new cultivar 'RUITSWEET' are similar to the parent in most horticultural characteristics. However the new variety, 'RUITSWEET' differs from the parent in the following characteristics:

1. Shorter branches.
2. Thinner branches.
3. Sturdier branches.
4. More branches.

COMMERCIAL COMPARISON

'RUITSWEET' is best compared to the seed parent.

BRIEF DESCRIPTION OF THE PHOTOGRAPHS

Figure 1:
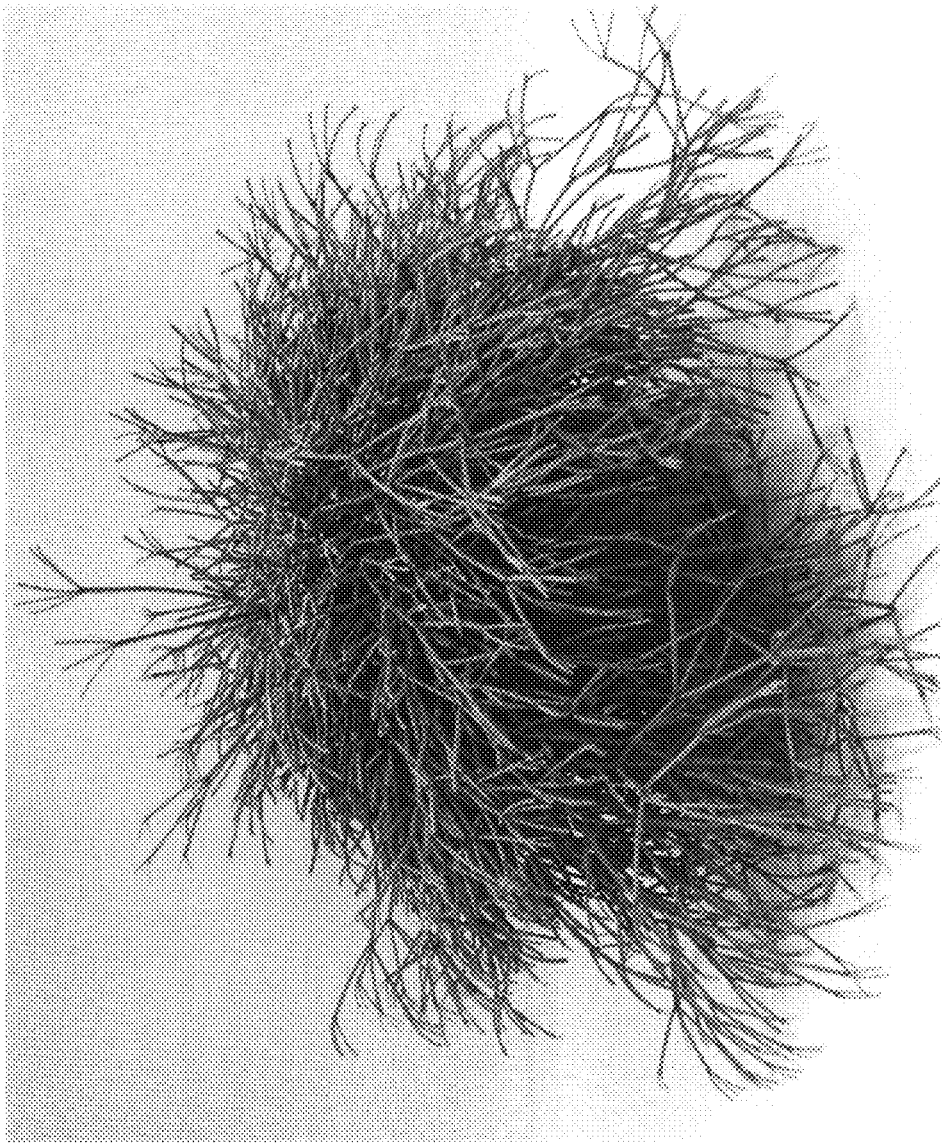

The accompanying photograph in FIG. 1 illustrates in full color a typical plant of 'RUITSWEET' grown in a commercial greenhouse in Nieuwerkerk, Netherlands. The plant is 6 months old from a rooted cutting, in a 13 cm pot.

Figure 2:
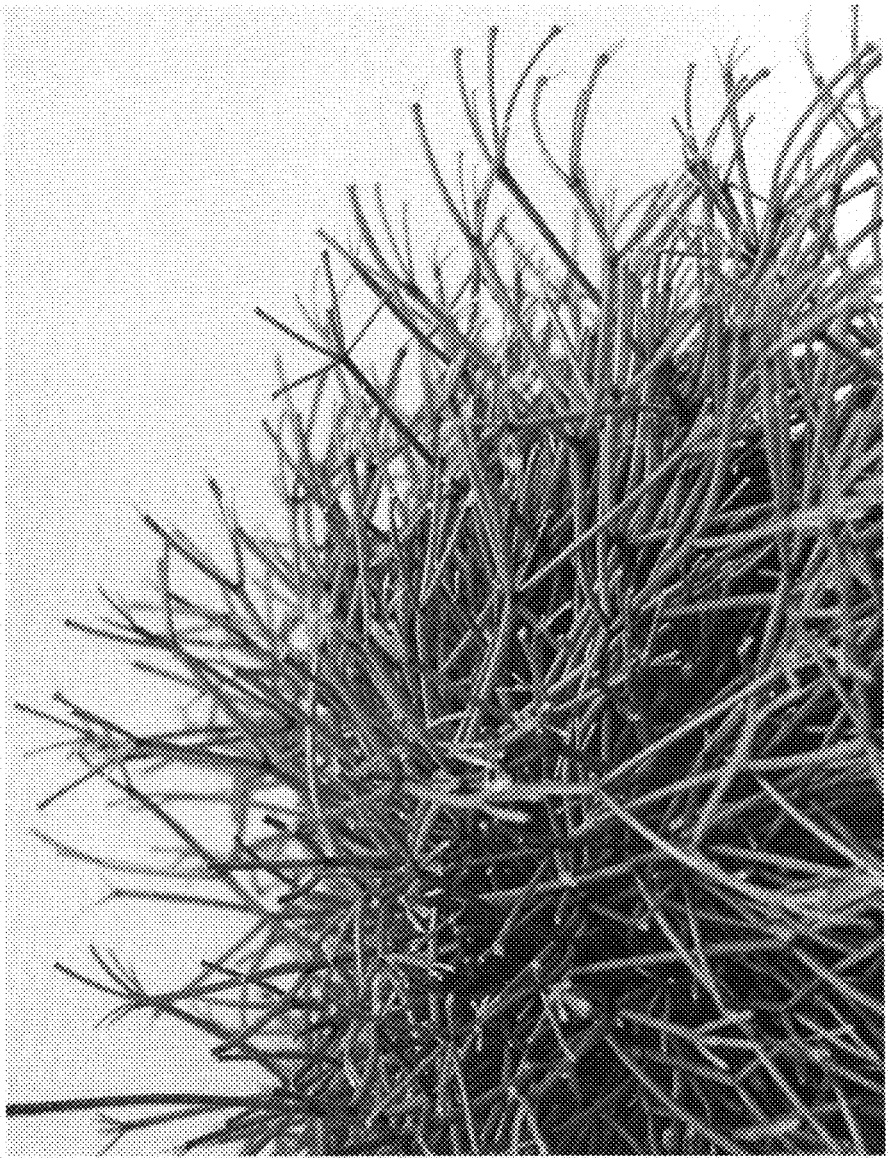

FIG. 2 is a closeup of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a typical plant of 'RUITSWEET' grown in a commercial greenhouse in Nieuwerkerk, Netherlands. The plant is 6 months old from a rooted cutting, in a 13 cm pot. Temperatures ranged between 20° C. and 32° C. during the day 10° C. and 20° C. at night. No supplemental lighting was given. Measurements and numerical values represent averages of typical plant types.

Botanical classification: *Rhipsalis clapata* 'RUITSWEET'.

PROPAGATION

First propagation method: Vegetative cuttings.
Type of propagation typically used: Vegetative cuttings.
Root description: Fibrous.

PLANT

Growth habit: Mounding, then weeping.
Height: Approximately 10 cm to top of highest leaf.
Plant spread: Approximately 12 cm in an 11 cm pot.
Growth rate: Moderate.
Stem: No stem, all lateral branches.
Branching characteristics:

*Quantity lateral branches*.—Approximately 150 on an 11 cm pot.
*Diameter*.—Average 0.25 cm.
*Length*.—Average range 1.5 to 3.0 cm.
*Angle of attachment*.—Average angle about 45°.
*Aspect*.—Straight.
*Branch texture*.—Glabrous.
*Internode texture*.—Minute, less than 1 mm soft pubescence.
*Internode length*.—Average range about 1.0 cm to 4.0 cm.
*Color*.—Immature: Nodes colored near RHS Greyed-Red 181B. Young branches near RHS Yellow-Green 151A, flushed with RHS Greyed-Red 178C. Mature: Near RHS Green 146C.

FOLIAGE

Leaf: True leaves are appressed scales. Highly reduced on this variety to either none at the node or miniscule.

*Arrangement*.—Rosette.
*Average length*.—Approximately 1 mm.
*Average width*.—Approximately 0.5 mm.
*Shape of blade*.—Narrow deltoid.
*Apex*.—Acute.
*Base*.—Blunt.
*Margin*.—Entire.
*Quantity of leaves per node*.—Typically 2.
*Color*.—Near RHS Yellow-Green 150D.
*Venation*.—Reduced structure is too minute to measure.

FLOWER

Bud production and flower production not been observed to date.

REPRODUCTIVE ORGANS

Not observed due to lack of flower production.

OTHER CHARACTERISTICS

Disease and pest resistance: Plants resist aphid, caterpillars and thrips. Neither resistance nor susceptibility to normal diseases of *Rhipsalis* has been observed in this variety.

Drought tolerance and temperature tolerance: Drought tolerant succulent. Tolerates a temperature range from approximately 5° C. to approximately 40° C.

Fruit/seed production: Fruits and seeds have not been observed to date.

What is claimed is:

1. A new and distinct cultivar of *Rhipsalis* plant named 'RUITSWEET' as herein illustrated and described.

* * * * *